United States Patent [19]
Lee et al.

[11] Patent Number: 5,891,184
[45] Date of Patent: Apr. 6, 1999

[54] FILTERING TELEMETRY SIGNALS EMITTED BY A MEDICAL DEVICE

[75] Inventors: Chik Yam Lee, Arcueil; Herve Deschamp, Suresnes, both of France

[73] Assignee: ELA Medical, S.A., Montrouge, France

[21] Appl. No.: 868,519

[22] Filed: Jun. 4, 1997

[30] Foreign Application Priority Data

Jun. 4, 1996 [FR] France .................................. 96-06823

[51] Int. Cl.⁶ ....................................................... A61N 1/08
[52] U.S. Cl. ................... 607/60; 607/32; 607/31
[58] Field of Search ................... 607/31, 32, 60, 607/65; 128/901

[56] References Cited

U.S. PATENT DOCUMENTS

| | | | |
|---|---|---|---|
| 4,243,045 | 1/1981 | Mass ......................................... | 128/901 |
| 4,681,111 | 7/1987 | Silvian ....................................... | 128/419 |
| 4,864,590 | 9/1989 | Arnon et al. ............................... | 375/14 |
| 4,944,299 | 7/1990 | Silvian ....................................... | 128/419 |
| 5,181,228 | 1/1993 | Takatori ..................................... | 375/103 |

FOREIGN PATENT DOCUMENTS

| | | | |
|---|---|---|---|
| 0 607 638 A2 | 7/1994 | European Pat. Off. ........ | A61N 1/372 |
| WO 91/16696 | 10/1991 | WIPO ............................. | G08C 19/02 |

OTHER PUBLICATIONS

Biomedizinische Technik vol. 29, No. 9, sep. 1984, Berlin, DE pp. 202–207, XP002025596 Schsldach et al. (Abstract in English).

Primary Examiner—William E. Kamm
Assistant Examiner—Kennedy J. Schaetzle
Attorney, Agent, or Firm—Orrick, Herrington & Sutcliffe LLP

[57] ABSTRACT

A device for filtering signals emitted by a medical device, principally an active implanted medical device. The device (26) receives an input that is a signal delivered by a circuit (16–24) that receives signals emitted by a medical device (10) in the form of a magnetic induction, in which the medical device has a metallic housing or case. A compensation stage (42) also is provided, having in the frequency domain a transfer function in the form:

$$\Psi(f) = 1 + j\frac{f}{f_c}$$

where $f_c$ is a chosen parameter according to the geometry and the material of the metallic case of the medical device (10), and where $j=\sqrt{-1}$. The device is useful with medical devices that emit sequences of messages formed by symbols belonging to an alphabet of n symbols ($n \geq 2$), the compensation stage being able to reduce the rate of inter-symbol interference of collected signals that are applied to it.

14 Claims, 1 Drawing Sheet

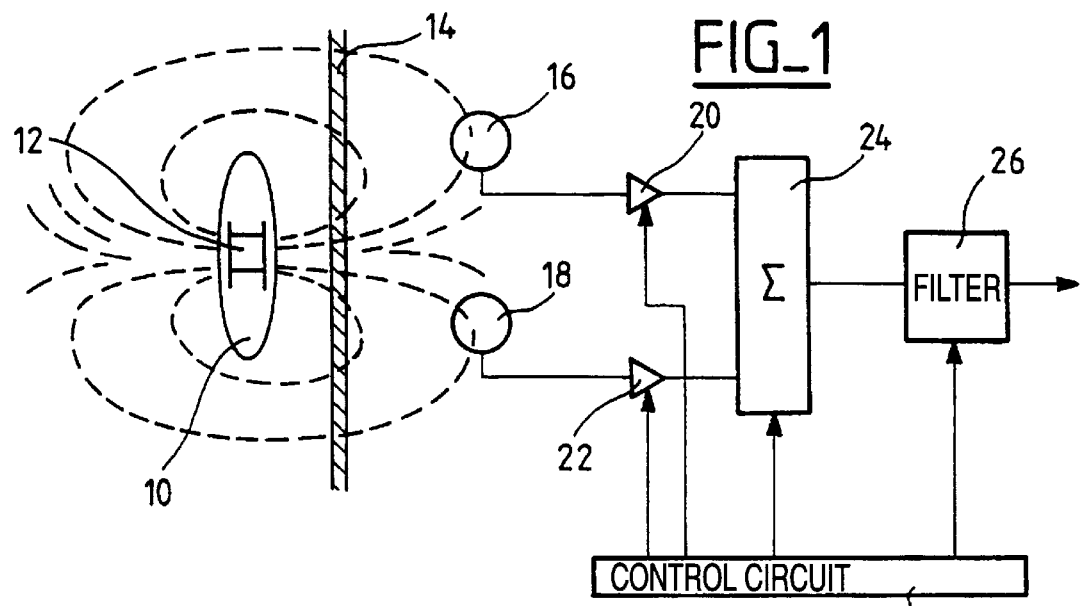
FIG_1
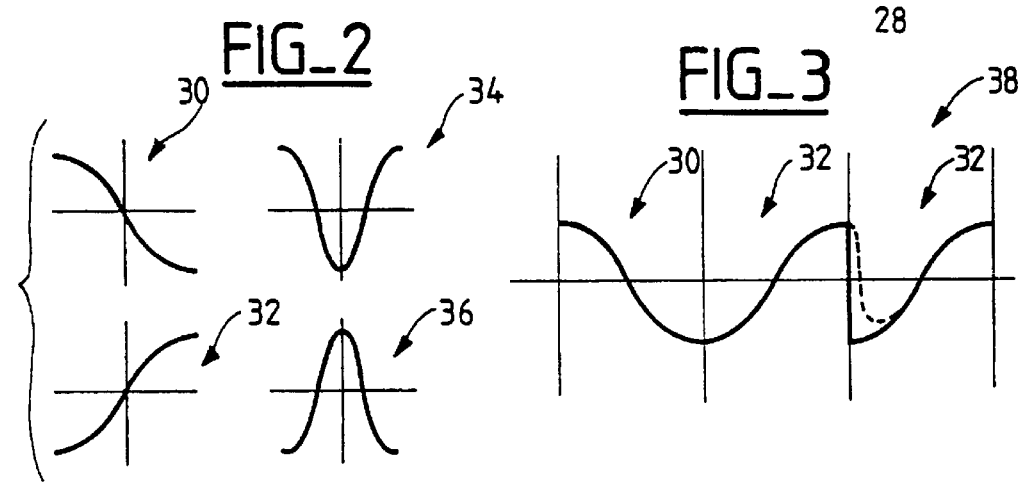
FIG_2   FIG_3
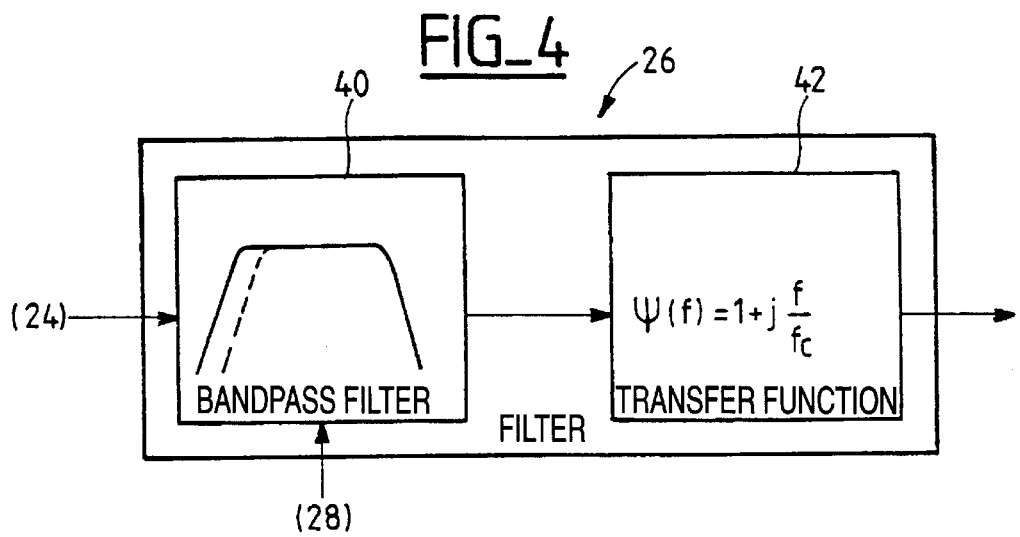
FIG_4

FILTERING TELEMETRY SIGNALS EMITTED BY A MEDICAL DEVICE

FIELD OF THE INVENTION

The present invention concerns medical devices, principally active implanted medical devices such as those defined by the Jun. 20, 1990 directive 90/385/EEC of the European Community Counsel, and more particularly the collection of signals emitted during communication sequences between the medical device and an external control console.

BACKGROUND OF THE INVENTION

Active implanted medical devices comprise, for example, cardiac pacemakers, defibrillators, neurological machines, pumps for dispensing medical substances, and cochlear implants (collectively hereinafter referred to as "implants"). Although the following description refers to active implanted medical devices, the present invention, is not limited to active implanted medical devices, but it applies as well to medical devices which are not implanted (for example, devices carried or worn by the patient) and medical devices which are not active (for example, those devices, whether or not implanted, that do not have a source of energy, and which use a portion of the energy of the interrogation signal that is applied to the device, for the emission of messages to the exterior. These devices, once put in place (principally by implantation), are programmed from the exterior by means of a remote or distant console which is commonly called a "programmer". The verification of parameters of the implant and/or the transmission of information recorded by the implant are typically realized by electromagnetic inductive coupling, called "telemetry"in the technique in question. The programmer is typically supplied with a receiver or head that is placed in face of, that is in proximity to the site of, the implant. This head comprises an antenna or coil that collects the magnetic field emitted from or generated by the implanted device by which data or information is communicated.

When one operates a transmission of information from the implant to the programmer, the nature of the material used in the construction of the housing of the implant (also known as the "case" as it will be hereinafter referred) should be taken into account. Indeed, the case is generally formed of a metallic material such as titanium. This material, due to its electrically conductive properties, has a current induced as a result of a transmission of data or information by telemetry, i.e., the main magnetic field or the useful signal. The induced current operates to re-emit a compensatory (parasitic) magnetic field that combines with, and has the effect of a low-pass filter on, the main magnetic field. This low-pass filtering introduces a distortion of a type known as "inter-symbol interference" or "inter-symbol jamming" or "longitudinal interference". It has, as an effect, in a given sequence of symbols (units of information), an overflow of one symbol on the following symbol. For adjacent symbols, this distortion becomes significant and can introduce ambiguities during the decoding of symbols.

OBJECTS AND SUMMARY OF THE INVENTION

It is, therefore, an object of the invention to overcome this limitation by proposing a circuit that compensates for the distortion introduced by the case of a medical device, significantly reducing principally the inter-symbol interference and allowing thereby a significant increase of the transmission rate of signals, or alternatively the simplicity with which one is going to decode symbols.

To this end, the present invention concerns providing the programmer with a filtering device receiving at an input a signal delivered by a circuit for receiving the emitted signal, in the form of a magnetic induction, by a medical device having a metallic case, and is characterized in that it comprises a stage of compensation possessing, in the frequency domain, a transfer function of the form:

$$\Psi(f) = 1 + j\frac{f}{f_c}$$

$f_c$ is a parameter chosen according to the geometry and the material of the metallic case of the medical device, and where $j = \sqrt{-1}$.

The invention is applied in a particularly advantageous manner in the environment where the medical device emits messages formed of elementary symbol sequences belonging to an alphabet of n symbols (30–36), with $n \geq 2$, the compensation stage then being a filter stage able to reduce the rate of inter-symbol interference of collected signals that are applied to it.

Preferably, the present invention also comprises a band-pass filter stage having high and low cutoff frequencies that are chosen according to the range of frequencies of the signals emitted by the implanted device; more preferably the high cut-off frequency and/or the low cutoff frequency can be adjustable.

BRIEF DESCRIPTION OF THE DRAWINGS

Others characteristics of and advantages of the present invention will appear to a person of ordinary skill in the art in view of the following detailed description, made with reference to annexed drawings, in which:

FIG. 1 is a block diagram of the implant and the reception and processing circuit in the programmer in accordance with a preferred embodiment of the present invention;

FIG. 2 illustrates an example of an alphabet of four symbols to realize the modulation of the signal emitted by the implant;

FIG. 3 illustrates the phenomenon of inter-symbol interference in the environment of the utilization of the alphabet of the FIG. 2, in the absence of filtering according to the invention; and FIG. 4 is a block diagram showing the two filtering stages of FIG. 1.

DETAILED DESCRIPTION OF THE DRAWINGS

Referring to FIG. 1, the reference 10 designates an implant, that is to say an "active implanted medical device" in the broad sense defined above, operating in a patient. Implant 10 contains in memory information that are, for example, transported by the magnetic induction provoked by the passage of oscillating currents in an emitting coil 12, thus transmitting "by telemetry"the information beyond the cutaneous barrier 14. Signals thus emitted, that are essentially magnetic in nature as explained above, are collected by the receiver head of a programmer, that is, for example, a device of a type comparable to that described in EP-A-0 661 077 (and the corresponding U.S. application Ser. No. 08/363,742, now issued as U.S. Pat. No. 5,674,265) to which one will be able to refer for further details on the manner in which signals are collected and processed (but in a manner not restrictive with regard to the invention). U.S. application Ser. No. 08/363,742 is copending and commonly assigned, and is hereby incorporated herein by reference in its entirety. As described herein, one can extract from the total signal carried in the form of the magnetic field the useful signal component (the main magnetic field) by eliminating almost totally the parasitic signal component (the parasitic magnetic field).

To this purpose, at least two distinct receiving coils are provided, although a plurality of receiving coils could be used. More specifically at least a collector coil 16 and a compensation coil 18, each collecting induced magnetic fields and producing therefrom corresponding voltages which are applied on respective amplifiers 20 and 22. Amplifiers 20 and 22 are each provided with a variable gain. The respective amplifier outputs then are then combined in a summing stage 24 in a conventional manner. By an appropriate gain adjustment of amplifiers 20 and 22, the output of the summing stage 24 is a signal consisting essentially of the useful signal as the sole component.

The invention also provides a circuit 26 to process the useful signal in a manner to reduce certain forms of distortion, as will be described below. Circuit 26, and also the other processing circuits and signals of the programmer, can be realized in different manners, for example, in an entirely analog circuit manner, or with digital circuits, including microprocessor based circuits driven by software for performing the functions described herein.

The different functional blocks are controlled by a control circuit 28 which can advantageously comprise a microcalculator allowing to adjust the parameters of the different elements of the circuit to obtain the desired results. In any event, the hardware realization of these circuits is in no manner restrictive with regard to teachings of the invention, and may be implemented in any manner known to a person skilled in the art; for this reason, these hardware aspects are not be described more in detail.

One is now going to explain the phenomena of distortion that can be remedied by the circuit of the present invention. The case of the implant 10 is typically realized in a metallic material, typically titanium or a titanium based alloy. It should be understood, however, that the invention is not limited to this particular material of the case. As the magnetic induction is produced by a source (emitting coil 12) that is enclosed in a conducting case, the useful signal, in the meaning indicated above (that is to say the signal separate from any parasitic signals coming from magnetic sources of external origin), is going to be found to be disturbed. This disturbance will provoke an attenuation in the high frequency spectrum of the frequency domain, that is to say, result in a low-pass filtering.

The particular inter-symbol interference phenomenon caused by this low-pass filtering is described with reference to FIGS. 2 and 3. One will take the example of a quaternary modulation realized by combination of a binary phase modulation and a binary frequency modulation. It is noted that the problem similarly exists in comparable terms, for example, for a phase modulation phase of four states, or for other types of modulations. One thus defines a "alphabet" of four "symbols" 30, 32, 34 and 36, as illustrated in FIG. 2. Symbols 30, 32 on the one hand, and 34, 36 on the other hand, are emitted at two different frequencies, for example, 8 and 16 kHz. Symbols 30, 34 on the one hand, and 32, 36 on the other hand, are respectively emitted 180° out of phase.

We consider, for example, as illustrated in FIG. 3, the sequence 38 formed of three successive symbols 30, 32 and 32. If the transition between symbols 30 and 32 is made without a solution for continuity, there is a significant and abrupt discontinuity of the signal level, corresponding to an abrupt transition from a positive level to a negative level in the transmission of the two consecutive symbols 32 (38). This abrupt transition is translated in the frequency domain by the production of high order harmonic components. But, as explained above, the presence of the titanium case plays the role of a natural low-pass filter that prevents the transmission of these high order harmonics, thereby introducing a distortion of the signal. As a result, the transmission of symbols 30, 32, 32 will in reality, take the form illustrated in dotted lines on FIG. 3.

If one compares FIGS. 2 and 3, one notices that the waveform actually emitted from the implant, and, therefore collected by the programmer, is a waveform of a shape that is between that of the symbols 32 and 34. This phenomenon is known by the name of "inter-symbol interference" (or "longitudinal interference" or "inter-symbol jamming"), and is a phenomenon that can be more simply defined as the "overflow" or "crossover" of one symbol on the following symbol. This distortion is intrinsic to the signal emitted by the coil 12, and appears therefore on the useful signal, that is to say the "pure" signal from which all parasites of external origin have been removed. In other words, any improvement of the signal/noise ratio in the circuits for the reception and processing of the signal will have no impact on this type of distortion. Further, if this type of distortion reaches an excessive level, it can introduce ambiguities and errors in the transmission of symbols. The third symbol of the sequence 38 shown in FIG. 3 is able, for example, to be incorrectly interpreted as a symbol 34 and not as a symbol 32. Moreover, the effect of the natural low-pass filtering of the titanium, intrinsic to the material, is all the more emphasized that the frequency of the signal is high.

The invention is therefore directed to reduce this phenomenon, with the main consequences (among others) being, on the one hand, the considerable reduction of the inter-symbol interference and therefore the diminution, or the suppression, of the risk of ambiguity during the decoding of the symbols. The invention is based on the recognition by the inventors that, when a magnetic induction is produced by a source that is enclosed in a conducting case, this induction is multiplied in the frequency domain to the exterior of the case by a transfer function of the form:

$$\chi(f) = \frac{1}{1 + j\frac{f}{f_c}}$$

where $f_c$ is a parameter depending on the geometry and the material of the metallic case, and where $j = \sqrt{-1}$.

To restore, from the useful component of the collected signal, a signal corresponding to the signal as though not disturbed by the case, one can foresee an element whose transfer function $\psi(f)$, which is the inverse of $\chi(f)$, and which will compensate for the latter:

$$\Psi(f) = 1 + j\frac{f}{f_c}$$

The device filter circuit 26 of the invention can be constituted, as illustrated with reference to FIG. 4, as a filter stage 40 of filtering, formed by a band-pass filter, followed by a compensation filter stage 42 implementing the transfer function $\psi(f)$.

The filtering stage 40 (which incidentally is not indispensable to the implementation of the invention, but does advantageously improve the efficiency) is a classic band-pass filter. Preferably, the filter 40 is programmable to adjust the high and low cut-off frequencies by appropriate commands issuing from control circuit 28. Such a programmable circuit allows principally to take into account automatically useful signals emitted on different carrier frequencies. For example, it will allow the programmer to read data from classic implant functioning at carrier frequencies of 8 to 16 kHz, as well as the newer type implants functioning at higher frequencies, e.g., 128 kHz, as well as data arising from implants of different manufacturers.

The band-pass filter 40 is desirable to improve the signal/noise ratio of the signal being processed by eliminating undesirable components situated out of the normal passband. Low and high cut-off frequencies can be, for example, 90 kHz and 160 kHz respectively, to process a useful signal whose carrier frequency is 128 kHz (for example, with newer type implants with higher carrier frequency), or 4 kHz and 160 kHz respectively, to process a useful signal with a carrier frequency going from 8 kHz to 16 kHz, as with current typical implants.

The signal thus filtered by the stage 40 is then transmitted to the compensation stage 42 applying the transfer function ψ(f), thereby restoring the profile either exactly or approximately, by restoring the form (either exactly or approximately) to what the former would have if it had been emitted by a coil 12 not enclosed in a metallic case.

One skilled in the art will appreciate that the present invention can be practiced by other than the described embodiments, which are presented for purposes of illustration and not of limitation.

We claim:

1. A filter (26), for receiving at an input a first signal delivered by a receiving circuit (16–24) in response to a second signal emitted by a medical device (10), the second signal being in the form of a magnetic induction, said medical device comprising a metallic case having a material and a geometry, the filter characterized in that it comprises a compensation stage (42) having in the frequency domain a transfer function of the form:

$$\Psi(f) = 1 + j\frac{f}{f_c}$$

where $f_c$ is a parameter chosen according to the geometry and the material of the metallic case of the medical device (10), and where $j=\sqrt{-1}$.

2. The filter of claim 1, in which the medical device emits messages having sequences formed of elementary symbols belonging to an alphabet of n symbols (30–36), $n \geq 2$, wherein the compensation stage operates to reduce the rate of inter-symbol interference of collected signals that are applied to it.

3. The filter of claim 1, wherein the second signal has at least one carrier frequency, further comprising a band-pass filter stage (40) having a high cutoff frequency above said at least one carrier frequency and a low cutoff frequency below said at least one carrier frequency, the bandpass filter being interposed between said second signal and the compensation stage.

4. The filter of claim 3, further comprising a control circuit operable to adjust the bandpass filter stage in which at least one of the high cutoff frequency and the low cutoff frequency is an adjustable frequency.

5. In a programmer for use with a medical device having a metallic case of a geometry and a material, and emitting a signal by magnetic induction, which signal is disturbed by transmission through said metallic case, apparatus for restoring the disturbed transmission signal comprising a compensation filter having in the frequency domain a transfer function operable to invert the disturbance introduced by transmission of the signal through the metallic case.

6. The apparatus of claim 5 wherein the metallic case interposes a low pass filter characteristic and the transfer function further comprises:

$$\phi(f) = 1 + j\frac{f}{f_c}$$

wherein $f_c$ is a parameter chosen according to the geometry and material of the case, and $j=\sqrt{-1}$.

7. The apparatus of claim 5, wherein the emitted signal has at least one carrier frequency, and further comprising a band pass filter having a high cutoff frequency above said at least one carrier frequency and a low cutoff frequency below said at least one carrier frequency, said band pass filter being interposed between said disturbed transmission signal and said compensation filter.

8. The apparatus of claim 7 further comprising:

a first receiving coil having a first output;

a second receiving coil having a second output; and a summing circuit having an input for receiving the first and second outputs, and a summed output corresponding to a sum of the first and second outputs; wherein the summed output is input to said band pass filter.

9. A method of filtering a signal corresponding to a magnetic induction emission from a medical device distorted by transmission through a metallic case, the signal being received by a programmer, comprising:

providing a transfer function in the frequency domain that is the inverse of the distortion introduced by transmission of the magnetic induction emission through said metallic case;

applying the transfer function to said signal, and restoring the signal to correspond to said magnetic induction emission prior to transmission through said metal case.

10. The method of claim 9 wherein the metallic case has a geometry and a material and a low pass filter characteristic, and the step of providing a transfer function further comprises providing a transfer function of the form:

$$\phi(f) = 1 + j\frac{f}{f_c}$$

wherein $f_c$ is a parameter chosen according to the geometry and material of the case and $j=\sqrt{-1}$.

11. The method of claim 10 further comprising band pass filtering said signal prior to applying said transfer function thereto.

12. The method of claim 11 wherein the magnetic induction emission has at least one carrier frequency and the step of band pass filtering further comprises providing a high cutoff frequency above said at least one carrier frequency and a low cutoff frequency below said at least one carrier frequency.

13. The method of claim 12 further comprising adjusting at least one of the high cutoff frequency and the low cutoff frequency.

14. The method of claim 9 further comprising providing said signal as a sequence of elementary symbols selected from an alphabet of n symbols, $n \geq 2$, so that applying said transfer function reduces the intersymbol interference in said signal.

* * * * *